a2 United States Patent
Zumsteg et al.

(10) Patent No.: US 8,801,724 B2
(45) Date of Patent: Aug. 12, 2014

(54) DEVICE FOR PLACING OR REMOVING JOINTS OR JOINT SOCKETS (75) Inventors: Lukas Zumsteg, Sulz (CH); Walter Moser, Kaufdorf (CH); Thomas Kilchenmann, Horgen (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 1060 days.

(21) Appl. No.: 11/571,226

(22) PCT Filed: May 30, 2005

(86) PCT No.: PCT/EP2005/005802
§ 371 (c)(1),
(2), (4) Date: Jul. 26, 2007

(87) PCT Pub. No.: WO2005/122970
PCT Pub. Date: Dec. 29, 2005

(65) Prior Publication Data
US 2007/0270783 A1 Nov. 22, 2007

(30) Foreign Application Priority Data

Jun. 22, 2004 (DE) .......................... 10 2004 030 031
Aug. 31, 2004 (DE) .......................... 10 2004 042 183

(51) Int. Cl.
*A61B 17/56* (2006.01)
*A61B 17/88* (2006.01)

(52) U.S. Cl.
USPC .............................................. 606/99; 606/91

(58) Field of Classification Search
USPC ....................... 606/1, 80–81, 90–91, 99, 100; 623/22.11–22.12, 22.21; 24/270
See application file for complete search history.

(56) References Cited

U.S. PATENT DOCUMENTS

| 4,382,570 | A | * | 5/1983 | Craig | 248/74.3 |
| 5,098,437 | A | * | 3/1992 | Kashuba et al. | 606/89 |
| 5,169,399 | A | * | 12/1992 | Ryland et al. | 606/91 |
| 5,320,625 | A | * | 6/1994 | Bertin | 606/91 |
| 5,351,368 | A | * | 10/1994 | Borst | 24/270 |
| 5,474,560 | A | | 12/1995 | Rohr, Jr. et al. | |
| 5,540,697 | A | * | 7/1996 | Rehmann et al. | 606/91 |

(Continued)

FOREIGN PATENT DOCUMENTS

DE    43 37 936 A1    5/1995
DE    197 23 620       12/1998

(Continued)

OTHER PUBLICATIONS

Examination Report in corresponding German Application No. 10 2004 042 183.8, mailed Feb. 4, 2004.

(Continued)

*Primary Examiner* — Nicholas Woodall
*Assistant Examiner* — Larry E Waggle, Jr.
(74) *Attorney, Agent, or Firm* — Krieg DeVault LLP (57) ABSTRACT A tool for placing or removing joint sockets of an artificial joint, especially a hip joint, and a tool for placing or removing an artificial joint, has a handle, a joint socket or joint receiver or holder, and a connecting element arranged between the handle and the joint socket or joint holder. The connecting element comprises an arcuate portion in its longitudinal direction. A system for placing and removing joint sockets or joints using such a tool includes a position-determining and navigation device.

35 Claims, 4 Drawing Sheets

(56) References Cited

U.S. PATENT DOCUMENTS

| | | | |
|---|---|---|---|
| 5,571,111 A * | 11/1996 | Aboczky | 606/91 |
| 5,609,647 A | 3/1997 | Kalberer et al. | |
| 5,683,399 A | 11/1997 | Jones | |
| 6,540,737 B2 * | 4/2003 | Bacher et al. | 606/1 |
| 6,760,985 B2 * | 7/2004 | Wilson | 38/102.2 |
| 2003/0050645 A1 * | 3/2003 | Parker et al. | 606/99 |
| 2003/0229356 A1 * | 12/2003 | Dye | 606/99 |
| 2004/0097952 A1 * | 5/2004 | Sarin et al. | 606/102 |
| 2004/0215200 A1 * | 10/2004 | Tornier et al. | 606/91 |
| 2005/0085823 A1 * | 4/2005 | Murphy | 606/91 |
| 2005/0149050 A1 * | 7/2005 | Stifter et al. | 606/102 |
| 2005/0177172 A1 * | 8/2005 | Acker et al. | 606/99 |
| 2005/0228395 A1 * | 10/2005 | Auxepaules et al. | 606/91 |
| 2009/0171464 A1 | 7/2009 | Imhof | |

FOREIGN PATENT DOCUMENTS

| | | |
|---|---|---|
| DE | 103 06 793 | 12/2003 |
| DE | 103 60 390 A1 | 7/2005 |
| EP | 0 144 588 A2 | 6/1985 |
| EP | 0 169 978 | 2/1986 |
| WO | WO 2004-010882 | 2/2004 |

OTHER PUBLICATIONS

International Search Report for corresponding PCT Application No. PCT/EP2005/005802, mailed Sep. 19, 2005.

Search Report for PCT Patent Application No. PCT/EP2005/005802, mailed Sep. 19, 2005.

Examiner's First Report on Patent Application No. 2007237572 by Smith & Nephew Orthopaedics AG, mailed Mar. 13, 2012, 2 pages, Australian Government IP Australia.

* cited by examiner

DEVICE FOR PLACING OR REMOVING JOINTS OR JOINT SOCKETS

CROSS-REFERENCE TO RELATED APPLICATIONS

This Application is a US National Phase of the International Application No. PCT/EP2005/005802 filed May 30, 2005 designating the US and published in German on Dec. 29, 2005 as WO 2005/122970, which claims priority of German Patent Application No. 10 2004 030 031.3, filed Jun. 22, 2004, and to German Patent Application No. 10 2004 042 183.8, filed Aug. 31, 2004.

BACKGROUND OF THE INVENTION

1. Field of the Invention

The invention relates to a tool for placing or removing joint sockets, for placing or removing joints, and a position-determining device for ascertaining the position of a joint socket of an artificial joint or the position of an artificial joint.

2. Description of the Related Art

Joint sockets that are to be fixed in or on a bone of a recipient without cement generally consist of a metal shell for anchoring in or on the bone and a low-friction insert as counterpart to a complementary joint stem which is spherical in the case of many joints.

A known method of anchoring joint sockets implanted without cement is the clamping thereof in a bone bed that has been specifically prepared having smaller dimensions than the implant. The importance of that method, based on under-sizing of the prepared bone bed, can readily be demonstrated using the example of hip socket implants: that method is the most commonly used kind of cementless anchoring of hip socket implants. The next most frequently used method is fixation of the metal socket shell by means of bone screws which are separately positionable. A further kind of cementless anchoring comprises screw-in sockets in which fixation is effected by a thread of large surface area on the outer side of the shell, which thread is screwed into the bone.

Fixation by means of separate bone screws requires corresponding bores in the implant wall, through which the screws are introduced into suitable regions of the pelvis, for example into the roof of the acetabulum. The placement of the screws requires accessibility from different angles and a good view of the operating site.

The known screw-in sockets have a generally coarse, sharp-edged, self-tapping outer thread. The introduction of the implant accordingly requires an opening in the body that needs to be significantly larger than the implant in order to avoid injuries to the surrounding soft tissue structures caused by the sharp-edged, self-tapping thread.

The method of clamping a joint socket or a joint is known as a press-fit anchoring and is suitable particularly for implantation through small openings in the body, because the implants in question do not have projecting, sharp-edged anchoring elements, as in the case of, for example, the screw-in sockets described above. Furthermore, when that method is used, no additional working space is required for insertion of (separate) bone screws.

Depending upon the training of the surgeon and the indication in question, in accordance with the current state of the art joint replacement operations are performed through openings in the body which, after visualization and preparation of the joint parts to undergo surgery, allow secure implantation of the artificial joint components. In the case of customary surgical techniques, openings are created for that purpose in the body that are significantly larger than the artificial joint component. Through those openings in the body, the bone structures for anchoring the artificial joint components are worked on and the latter are finally implanted, with good visual monitoring.

The requirement for a minimum of surgical trauma, which is intended to result in as rapid as possible, pain-reduced rehabilitation of the patient, has led to the development of so-called minimally invasive surgical techniques. Minimally invasive joint implantations are highly desirable, because they offer a number of advantages over conventional operations. The relatively low degree of soft tissue traumatization means shorter wound healing times and accordingly more rapid, less painful rehabilitation of the patient. In addition, fewer functionally important structures are affected by the operation, which has a positive effect on the functionality of the joint provided with implants. Finally, such operations also offer the patient a cosmetic advantage, because a significantly smaller scar is formed.

The implantation of press-fit sockets in the case of conventional non-minimally invasive operations is effected by means of specific impaction instruments or tools, which allow secure implantation with the orientation of the socket being monitored. An example of such an instrument is known from U.S. Pat. No. 5,683,399. That instrument consists of a piece for coupling to the socket shell, a rectilinear rod-shaped intermediate piece for force transmission and a handle with an impact plate, by means of which the impaction force is applied by means of a hammer. It is important in such instruments that impaction with reliable monitoring of the orientation of the implant is ensured. In the case of the instrument according to U.S. Pat. No. 5,683,399, the coupling piece is clamped in the shell by means of a cone connection, the actuation of the cone connection being effected by means of a rectilinear spindle which extends inside the handle and the force-transmitting component.

If such an impaction tool were to be used in a minimally invasive surgical procedure, the surgeon would have a poor view of the operating site because the operating site would be concealed by the tool. Working on the operating site also requires instruments that allow the individual surgical steps to be carried out through a small opening in the body. In addition, surgical access has to be so selected that both joint parts can be implanted through the reduced-size opening in the body. Alternatively, implantations can also be carried out through two different openings in the body, but this is associated with increased risk in the positioning of the individual components, because the two components of a joint, that is to say the joint socket and the joint itself, have to be accurately positioned independently of one another. As can be inferred from what has been said above, particularly in the case of an operation on both joint parts through a reduced-size opening in the body, it is desirable to have a set of instruments that allows manipulation around the soft tissue structures, that is to say avoiding specific soft tissue structures. The implantation tools for the socket and the joint are particularly important in this respect, it being pointed out that no instruments suitable for performing such operations using a minimally invasive procedure are known.

SUMMARY OF THE INVENTION

The problem of the present invention is accordingly to provide a tool, but especially a system in the form of a position-determining and navigation device, for placing or removing joint sockets, especially sockets that are held in or on the bone of the recipient by means of a press-fit (so-called press-fit sockets), and also a tool or system for placing or removing artificial joints, especially hip stems, which provides the surgeon with the best possible view of the operating site, which renders position-determination and navigation in the operating site as simple as possible and which is thus also particularly suitable for minimally invasive surgery.

An important aspect of the invention is that in a tool for placing or removing joint sockets or joints, a connecting element, which is arranged between a handle and a joint socket receiver or holder, comprises an arcuate portion in its longitudinal direction. As a result of that structural feature, the surgeon has a good view of the operating site, so that joint sockets can reliably be removed and accurately fitted in place even in the case of a minimally invasive surgical procedure.

In a preferred embodiment, the connecting element comprises a T-shaped, double-T-shaped, I-shaped or rectangular profile. This imparts the necessary rigidity to the tool on the one hand, while on the other hand it has a relatively low weight, and accordingly only a small proportion of the acceleration forces of a hammer used to hammer in the joint socket being implanted is absorbed by the inert mass of the instrument.

Preferably, the dimensions of the cross-section of the profile of the connecting element vary longitudinally, so that the rigidity of the tool can be further improved. At locations of high stress, the tool is extremely stable, that is to say it has a large cross-section, whereas at locations of low stress and/or locations which would excessively restrict the surgeon's field of view, less material can be used, which, as already mentioned, additionally results in the (inert) mass of the tool being low.

In a further preferred embodiment, the connecting element has locations of reduced amassing of material and/or locations made of a material that does not correspond to the material from which the principal part of the connecting piece is made. That is to say, therefore, the connecting element can have, for example, openings in which it is also possible to provide struts, or it can have regions which are made of a different material, for example plastics material. The above-mentioned advantages of a tool having a low (inert) mass combined with rigidity that is a high as possible also apply to this embodiment.

The joint socket holder preferably has a stop forming a counterpart to the peripheral rim of the socket implant. The stop is either integrally joined to the connecting element or is releasably attached, especially by screws, at the end of the connecting element that faces the joint socket to be implanted. That ensures an optimum transmission of force to the socket implant. An integral join ensures a structurally simple embodiment, while a screw connection enables the tool to be taken apart, for example for the purpose of sterilization.

The joint socket holder preferably has one or more expanding element(s) engaging the inner side of the joint socket, which is(are) movable radially outwards against the inner side of the socket by means of an expanding mechanism comprising a cone or a wedge-in-wedge device. The expanding elements ensure that the joint socket is held securely in the tool for placement or removal of the socket, the expanding elements also ensuring that the socket implant is not able to twist, especially not in the equatorial direction. Once implantation is complete, it is also ensured that by virtue of the above-described expanding mechanism the tool can reliably be removed from the implanted joint socket without it being necessary to apply forces that would result in loosening of the seat of the socket. An analogous expanding mechanism is implemented in a preferred embodiment of a device for placing and removing joints, it being understood that in a device for the treatment of joints the expanding element(s) of course engage(s) the outer side of the joint in question.

The expanding mechanism is preferably connected to an actuating device which comprises a pull cable. A pull cable can be adapted in a simple way to the arcuate portion of the tool, the tool according to the invention having advantages in respect of easy sterilizability, particularly in comparison with flexible shafts or cardan shafts which are full of crevices and are difficult to clean.

Furthermore, the expanding mechanism is preferably connected to an actuating device such as, for example, a lever, which comprises an over-dead-centre mechanism or, alternatively or additionally, an eccentric mechanism. Reliable actuation of the expanding mechanism is thus ensured, it being virtually ruled out that unintentional expansion or contraction of the expanding mechanism will occur.

In a further preferred embodiment, the expanding element(s) is(are) movable into the expanded position against the action of a resilient element, especially against the action of a spring. This ensures a structurally simple arrangement. The resilient element or the spring exerts a force preferably in the radial direction, the expanding elements springing back automatically when the pull cable is released.

In a further preferred embodiment, the expanding element(s) has(have) radially outwardly or inwardly projecting projections, especially rib-like or bar-like projections, which in the expanded position form counterparts to corresponding or complementary radial recesses, especially equatorially extending grooves on the inner side of the joint socket or the outer side of the joint. This too is a structurally simple and therefore preferred embodiment.

Preferably, the radially outwardly projecting projections are part of an expanding ring which is divided by a slot. In a further preferred embodiment, the expanding ring is expandable radially outwards by means of a cone that engages the inner periphery and is connected to an actuating device. The expanding ring is preferably arranged on the underside, facing the interior of the socket, of the stop on the joint socket holder, which stop is especially of plate-like construction and co-operates with the peripheral rim of the joint socket, the expanding ring especially being mounted so as to be movable radially with respect to the stop. Preferably, the actuating device has an actuating lever pivotally mounted close to the handle, the bearing of which lever is eccentric relative to the connection of the pull cable on the actuating lever, so that the connection of the pull cable can be brought into two stable over-dead-centre positions relative to the bearing of the actuating lever, that is to say into a release position and into an expanded position. When the joint socket holder or joint holder is in the expanded position, the actuating lever can preferably be brought into a position parallel to the connecting element and can be fixed in that position by means of a locking mechanism. In a further preferred embodiment, the locking mechanism associated with the actuating lever comprises a bolt that can be engaged in a notch formed on the actuating lever, which bolt is biased into the locking position by a resilient element, especially a compression spring. The preferred exemplary embodiments described above are structurally simple embodiments of a tool according to the invention that ensure reliable actuation of the expanding mechanism and accordingly prevent unintentional release of the joint socket as well as unintentional expansion of the expanding mechanism.

The invention also includes the fundamental concept of using a tool according to the invention as part of a position-determining or navigation device. That ensures reliable and accurately fitted introduction of the joint socket, especially a hip socket, and of the joint, especially a hip stem, into the recipient bone. Furthermore, navigation in the patient during removal of a joint/joint socket and especially in the case of minimally invasive surgery is, of course, also significantly better in comparison with conventional surgical techniques.

Particularly from the standpoint of the above-described use, in a preferred embodiment, a tool according to the invention is associated with at least one marker which is detectable, especially contactlessly detectable, by means of an associated measurement value ascertainment system. It is thereby possible to ascertain the position of the tool in a simple way, which facilitates navigation during introduction or removal of a socket implant or an artificial joint.

In a further preferred embodiment, at least some of the markers have optical elements, especially retro-reflecting spheres. Optical elements, and especially retro-reflecting spheres, are easily detectable and require little outlay in terms of equipment. In a further preferred embodiment, at least one marker comprises magnetic and/or electromagnetic elements, which have the advantage that there is no need for direct visual contact between an associated measurement value ascertainment system and the markers themselves.

Preferably, at least one marker, but especially all the markers present, is(are) arranged on the handle, with the result that easy detectability of the markers is ensured.

In a further preferred embodiment, the central longitudinal axis of the joint socket holder or joint holder is in alignment with the central longitudinal axis of the handle. That ensures that when the joint socket or the joint or joint stem is being hammered in, no turning moment is exerted thereon. The basic concept of the invention includes the use of such a tool for placing or removing, especially hammering in, a hip socket or hip stem. The basic concept of the invention includes the actuation of the expanding mechanism for holding a joint socket or joint by the exertion of a force which changes direction at least to some extent in the course of its transmission. The transmission of force is effected, for example, in a pull cable which is curved, so that the force changes direction at least over certain regions of its transmission, i.e. its transmission path, and nevertheless acts on the expanding element. In other words, the basic concept of the invention includes the exertion of force on the expanding element, as well as, of course, on the joint socket or the joint, that take places not in a straight axial direction but, for example, over a curve or the like.

As already mentioned above, the basic concept of the invention includes both the use of a tool according to the invention for placing or removing a joint socket or a joint as part of a position-determining or navigation device, and, of course, a corresponding position-determining or navigation device as a system for placing and removing joint sockets is included in the basic concept of the present invention.

According to the invention, a position-determining device according to the invention for ascertaining the position of a joint socket of an artificial joint and/or the position of the artificial joint has a tool according to the invention for placing or removing joint sockets or joints, as described in greater detail above, as well as means for ascertaining the position and alignment of the tool and means for evaluating the acquired data. This ensures that the structure of such a position-determining device or a navigation device requires relatively little outlay in terms of equipment. It should be noted that in the context of a position-determining or navigation device a tool according to the invention can, of course, also be detected without markers mounted thereon. There come into consideration here, for example, on the one hand the detection of the position of the handle or the connecting element by suitable measures, which can be based, for example, on ultrasound waves, and the detection of the joint socket holder or of parts thereof, for example with the aid of its absorption or emission properties or spectra.

In a preferred embodiment, the position-determining device has, in addition, a memory for storing the acquired and/or evaluated data and/or for storing reference values and/or specific data in respect of the spatial position of the bone structure of the recipient. In a further preferred embodiment there is a comparison device which compares the actual position of the joint socket or the joint or joint stem and the position of a recess provided therefor or the desired position in the bone of the recipient and provides corresponding navigation directions. The possibility of storing the spatial position of the bone structure of the recipient and, additionally or alternatively, the above-mentioned comparison device ensures reliable navigation for the joint socket.

In a further preferred embodiment, the means for ascertaining the tool comprise means for ascertaining optical and/or magnetic and/or electromagnetic markers. Optical, magnetic or electromagnetic ascertainment ensures, on the one hand, reliable detection of the spatial position combined with, on the other hand, little outlay in terms of equipment. Preferably, the means for ascertaining the tool comprise a stereo-camera, which in the case of optical markers ensures a simply constructed device.

BRIEF DESCRIPTION OF THE DRAWINGS

The invention is described below in respect of further advantages and features by way of example and with reference to the accompanying drawings, wherein.

DETAILED DESCRIPTION OF THE PREFERRED EMBODIMENTS

Figure 1:
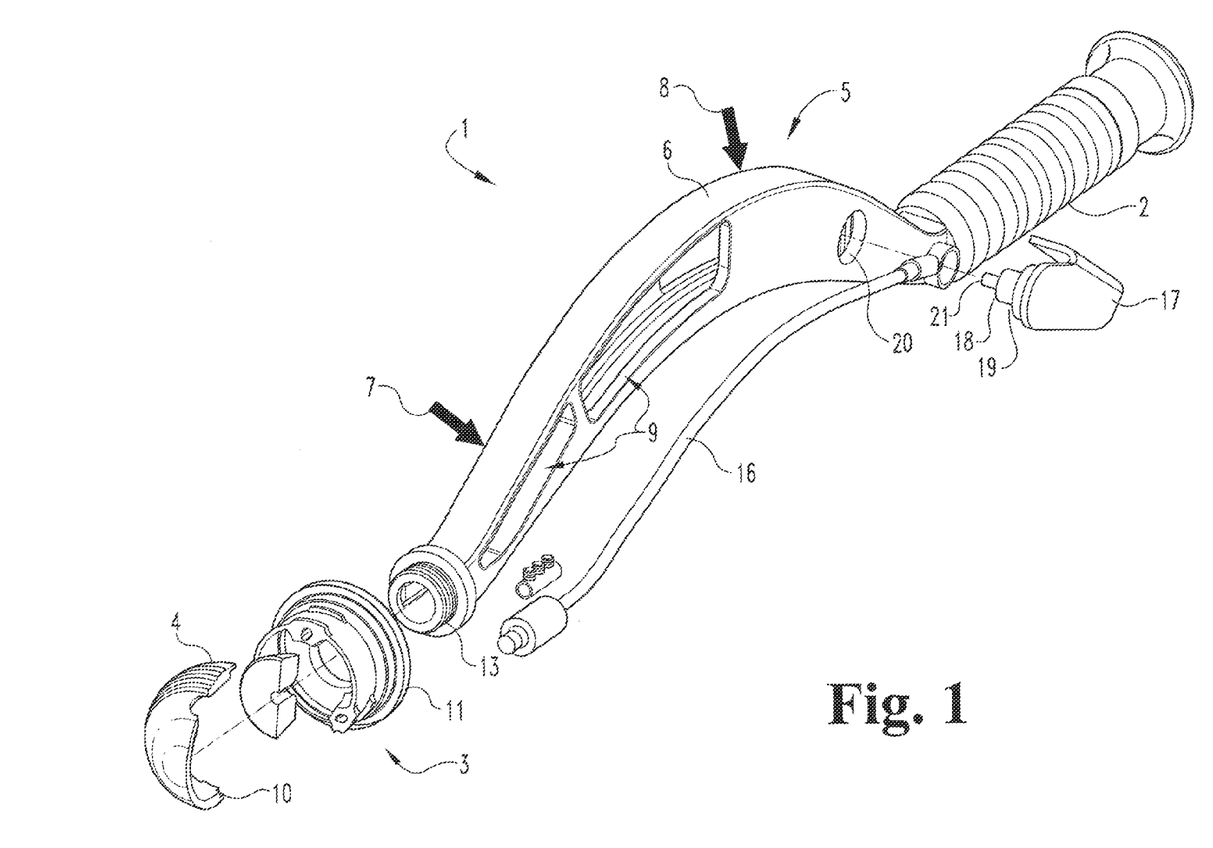
FIG. 1 shows a first preferred embodiment of a tool according to the invention for placing and removing joint sockets, as well as showing a joint socket, partly as an exploded view.

The first preferred embodiment of a tool 1 according to the invention for placing or removing joint sockets comprises a handle 2, a joint socket holder 3 (which is shown holding a joint socket 4 in FIGS. 2 and 3) and a connecting element 5, which is arranged between the handle 2 and the joint socket holder 3. The connecting element 5 comprises an arcuate portion 6 in its longitudinal direction. The connecting element 5 has a rectangular profile in this preferred embodiment, but a T-shaped, double-T-shaped or I-shaped profile would also be conceivable.

As can readily be seen from FIG. 1 when the connecting element 5 is viewed at the locations marked with arrows 7 and 8, the dimensions of the cross-section of the profile of the connecting element 5 vary longitudinally. The profile of the connecting element 5 is matched to the forces acting on the connecting element 5, so that the cross-section is larger at locations of high stress (for example at the location marked by arrow 8) than at locations of relatively low stress (for example the location marked by arrow 7).

The connecting element 5 also has locations of reduced amassing of material in the form of openings 9. If necessary, an embodiment is also conceivable in which a connecting element 5 has locations made of a material that does not correspond to the material from which the principal part of the connecting piece 5 is made. A simple realization thereof would be, for example, to fill the openings 9 with some other material, especially plastics material. This results in even greater stability combined at the same time with very good sterilizability of the tool 1.

Figures 2, 3:
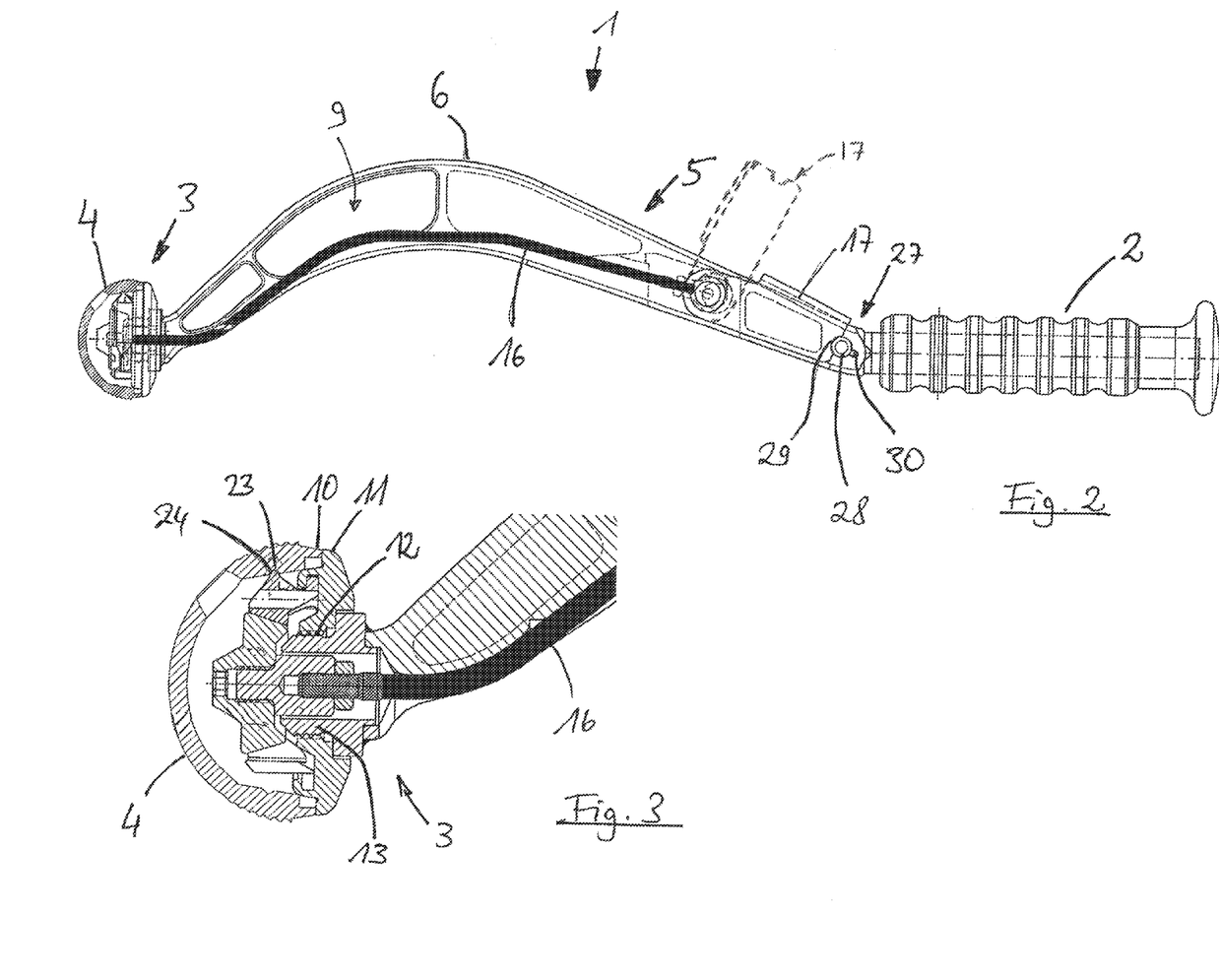
FIG. 2 is a sectional view of the preferred embodiment according to FIG. 1.
FIG. 3 is an enlarged view of a detail from FIG. 2, showing a joint socket holder of the tool according to FIGS. 1 and 2, including the joint socket being held.
Figure 4:
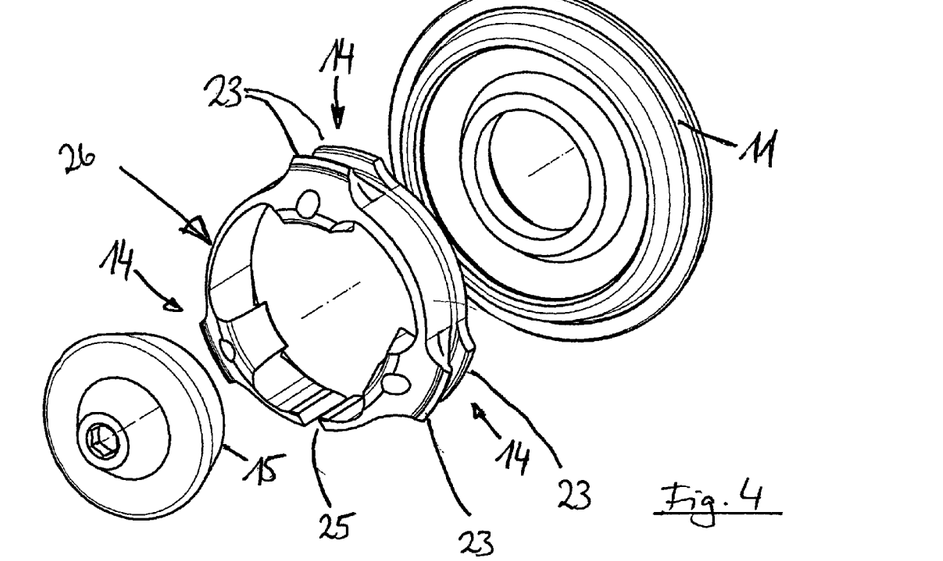
FIGS. 4+5 show the joint socket holder of the preferred embodiment, in each case in a perspective exploded view.
Figure 5:
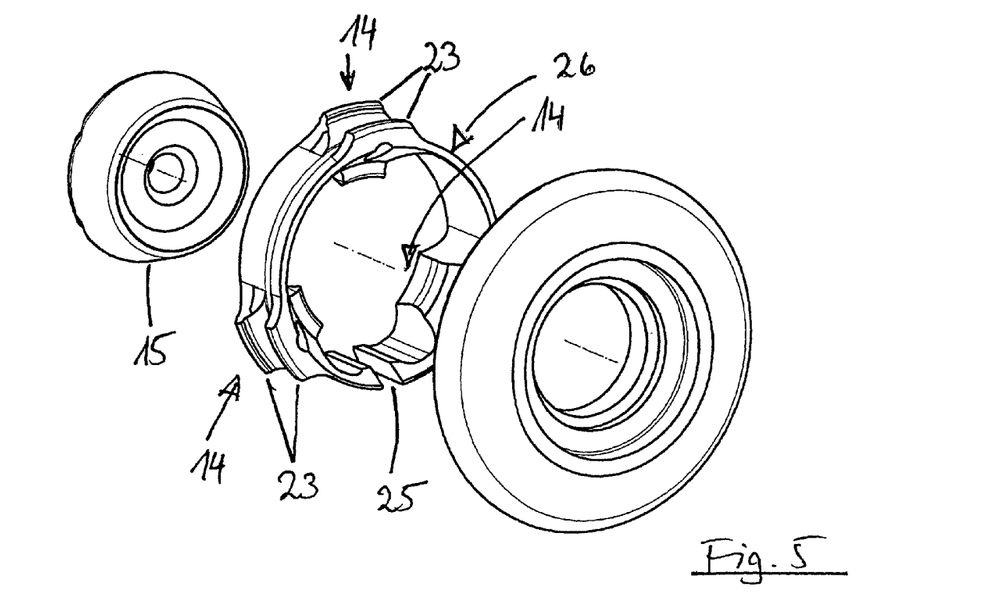

As can be seen especially from FIGS. 1 and 3, the joint socket holder 3 has a stop 11 forming a counterpart to the peripheral rim 10 of the joint socket 4. The stop 11 is releasably attached to the connecting element 5 at the end thereof facing the joint socket, this being effected by means of a thread 12, with which the stop is provided, and by means of a corresponding thread 13, with which the connecting element 5 is provided. The joint socket holder 3 also has, as can be seen most clearly from FIGS. 4 and 5, expanding elements 14 that engage the inner side of the joint socket 4, which expanding elements are movable radially outwards against the inner side of the joint socket 4 by means of an expanding mechanism comprising an internal cone 15. It should be mentioned at this point that as an alternative to a construction having a cone or internal cone 15 it would also be conceivable to use a wedge-in-wedge device for moving the expanding elements 14.

The expanding mechanism is connected to an actuating device which comprises a pull cable 16 (see especially FIGS. 1 to 3). The actuating device also has an actuating lever 17 which comprises an over-dead-centre mechanism and an eccentric mechanism. The eccentric mechanism is implemented by an eccentric bearing 18 for the connection of the pull cable 16 (see FIG. 1). Furthermore, the lever 17 is provided with a (centrically mounted) bearing ring 19, which engages in a complementary bearing eye 20 for the bearing ring 19. The lever 17 also comprises a centric bearing bolt 21 which engages a corresponding further bearing eye (not shown or not visible in the Figures) in the (rear) side wall of the connecting element 5.

The expanding elements 14 are movable into their expanded position against the action of a resilient element in the form of a radially acting spring. The expanding elements 14 have radially outwardly projecting projections 23 which are of rib-like or bar-like construction and in the expanded position form counterparts to complementary radial recesses in the form of equatorially extending grooves 24 on the inner side of the joint socket 4. The radially outwardly extending projections 23 are part of an expanding ring 26 which is divided by a slot 25. The expanding ring 26 is expandable radially outwards by means of the internal cone 15 engaging the inner periphery thereof, which internal cone is connected to the actuating device. The expanding ring 26 is arranged on the underside, associated with the interior of the joint socket, of the stop 11 on the joint socket holder 3, which stop is of plate-like construction and co-operates with the peripheral rim 10 of the joint socket 4. In this preferred embodiment, the expanding ring 26 is mounted so as to be radially movable relative to the stop 11.

The actuating device comprises, as already mentioned, the actuating lever 17 arranged pivotally mounted close to the handle 2, the bearing of which lever is eccentric relative to the connection of the pull cable 16 on the actuating lever 17, so that the connection of the pull cable 16 can be brought into two stable over-dead-centre positions relative to the bearing of the actuating lever 17, that is to say a release position and an expanded position. In the expanded position of the joint socket holder 3, the actuating lever 17 can be brought into a position parallel to the connecting element 5 and can be fixed in that position by means of a locking mechanism 27 (see FIG. 2). The locking mechanism 27 comprises a locking bolt 28, which can be engaged in a notch 29 formed on the actuating lever 17. The locking bolt 28 is biased into the locking position by a resilient element in the form of a compression spring 30.

As already described above, it will be understood that the scope of the invention also includes a tool for placing and removing artificial joints, that is to say, for example, hip stems. Such a tool is constructed analogously to the tool for placing or removing joint sockets and differs merely in the shape of the holder. Whereas the holder for joint sockets has the shape of a joint, the holder for a joint of course has the shape of a corresponding joint socket. That is to say, a holder for a joint socket is generally outwardly curved, while a holder for a joint surrounds the latter and is accordingly inwardly curved. The structure of one of the preferred embodiments or the preferred embodiments of the tool for placing joints is analogous to the structure of the tool for placing joint sockets.

Figure 6:
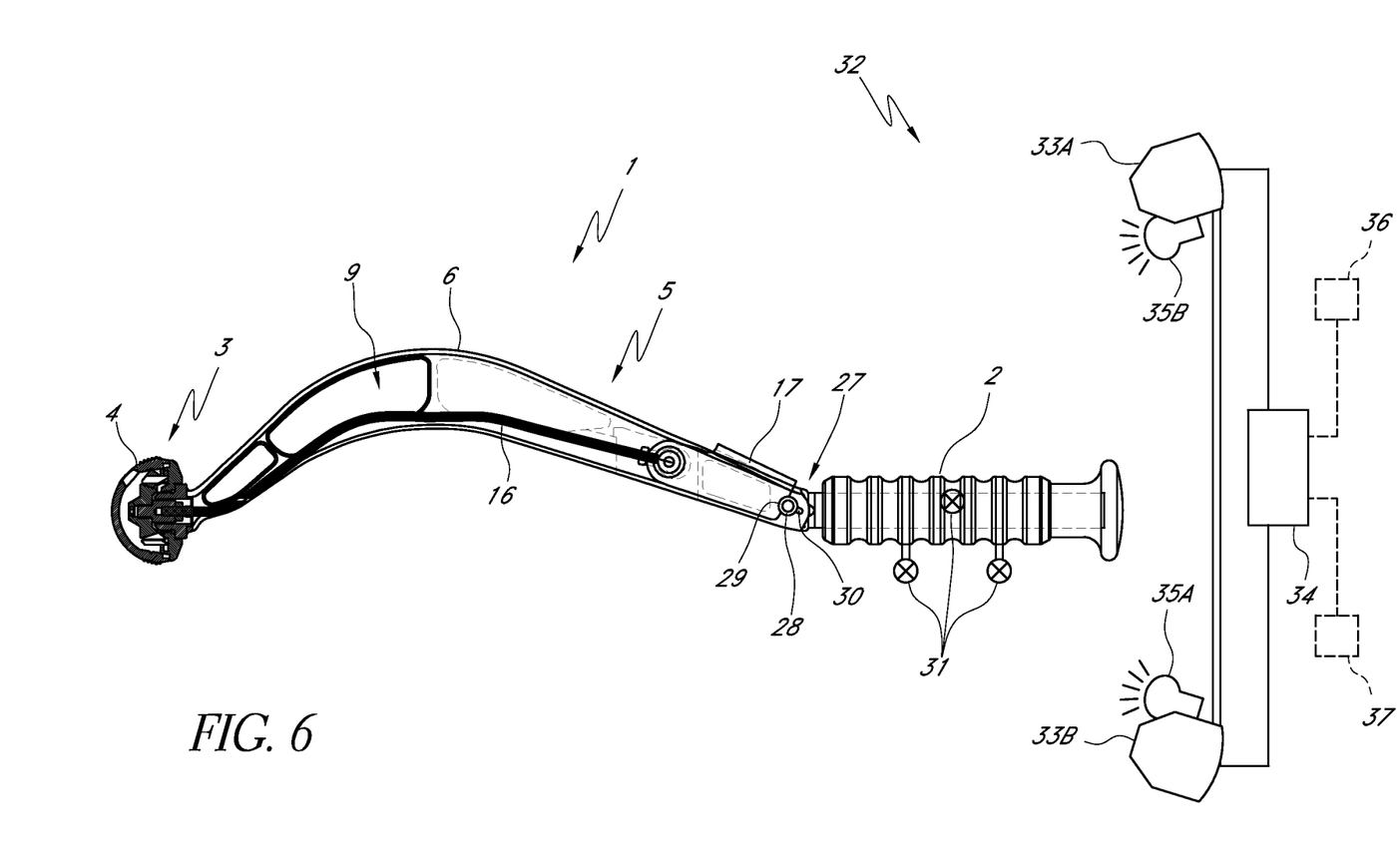
FIG. 6 shows a preferred embodiment of a position-determining device according to the invention, which comprises a second preferred embodiment of a tool according to the invention for placing and removing joint sockets.

As already mentioned, the basic concept of the invention includes the use of a tool according to the invention as part of a position-determining or navigation device 32. Furthermore, the basic concept of the invention also includes the provision of the device 32 itself, which is shown in FIG. 6. The tool 1, which is a component of the device 32 according to the invention, has all the features of the first embodiment described above, there additionally being provided on the tool 1 markers 31 which are detectable by an associated measurement value ascertainment system which is a component of the position-determining or navigation device 32.

In this preferred second embodiment, the detection of the markers 31 is effected contactlessly. The markers are in the form of optical elements, namely in the form of retro-reflecting spheres. It should be noted that, alternatively or additionally, magnetic and/or electromagnetic markers or markers having magnetic and/or electromagnetic elements are conceivable. They can be advantageous especially when the line of sight between a measurement value ascertainment system and a marker is blocked. If there is a clear line of sight, optical elements, especially in the form of retro-reflecting spheres, are a simple and cost-effective method of measurement value ascertainment. Furthermore, in the present exemplary embodiment, all the markers are arranged on the handle 2 of the tool. This ensures easy detectability. It should also be mentioned at this point that at the end of the handle remote from the connecting element there is a portion in the form of an impact plate which the surgeon can strike specifically with a hammer in order to be able to bring the joint socket 4 into its desired position.

In this second embodiment of the tool, as in the first embodiment of the tool, the central longitudinal axis of the joint socket holder 3 is in alignment with the central longitudinal axis of the handle 2. This ensures that, on impact, no turning moment is applied to the joint socket 4.

The device 32 also comprises means for ascertaining the position and alignment of the tool in the form of a stereo-camera, which is composed of two IR cameras 33A and 33B, and also means for evaluating the acquired data in the form of a computer unit 34. Suitable illumination of the markers 31 is provided by two IR illumination sources 35A and 35B. In the evaluating means in the form of the computer unit 34 there is implemented a special evaluating program which allows combined evaluation of light signals coming from the markers 31 to create a set of position data. The device also has a memory 36 for storing the acquired and/or evaluated data and/or for storing reference values and/or specific data in respect of the bone structure of the recipient as well as the spatial position of the bone structure of the recipient. By means of a comparison device 37, which compares the evaluated actual position of the tool 1, or the position of the joint socket 4 thereby determined, with the position of a recess in the bone of the recipient provided for the joint socket 4 and makes suitable navigation directions available to the surgeon on a monitor, the joint socket 4 is brought into its intended position.

Although the invention is described with reference to exemplary embodiments having fixed combinations of features, it also includes any conceivable further advantageous combinations of those features, as indicated, although not exhaustively, in the subsidiary claims. All the features disclosed in the application documents are claimed as being important to the invention, insofar as they are novel over the prior art individually or in combination.

What is claimed is:

1. A tool for placing or removing a joint socket of an artificial joint, the joint socket held on or in a bone of a recipient, said tool comprising:
    a handle;
    a joint socket holder comprising at least one expandable element comprising one or more radially outwardly projecting projections configured to engage an inner side of the joint socket, the expandable element movable radially outward against the inner side of the joint socket via the actuation of an expanding mechanism;
    an actuating device coupled to the at least one expandable element by a pull cable, the actuating device comprising a rotational center such that the expandable element can be moved by eccentrically bringing the pull cable to an over-dead-center-position over the rotational center when the actuating device is actuated, and can be brought into at least one other over-dead-center position; and
    a connecting element arranged between the handle and the joint socket holder,
    wherein the connecting element comprises an arcuate portion that extends along a longitudinal direction thereof.

2. The tool of claim 1, wherein the connecting element comprises a cross-sectional profile generally perpendicular to the longitudinal direction that is selected from the group consisting of a T-shaped, a double-T-shaped, an I-shaped, and a rectangular profile.

3. The tool of claim 2, wherein the dimensions of the cross-sectional profile of the connecting element vary longitudinally.

4. The tool of claim 1, wherein the connecting element has locations selected from the group consisting of locations of reduced amassing of material, locations made of a material that does not correspond to the material from which the principal part of the said connecting piece is made, and locations of reduced amassing of material and locations made of a material that does not correspond to the material from which the principal part of the said connecting piece is made.

5. The tool of claim 1, wherein the said joint socket holder comprises a stop forming a counterpart to a peripheral rim of the joint socket, the stop having a connection to the connecting element selected from the group consisting of integrally joined, releasably attached, and releasably attached especially by screws, said connection being at the end of the connecting element that faces the joint socket.

6. The tool of claim 5, wherein the one or more radially outwardly projecting projections comprise part of an expandable ring divided by a slot.

7. The tool of claim 6, wherein the expandable ring is expandable radially outward via a cone that engages an inner periphery of the expandable ring and is coupled to the actuating device.

8. The tool of claim 6, wherein the expandable ring, movably mounted in a radial direction relative to the stop, is arranged on the underside of the stop of the joint socket holder, facing the interior of the socket, the stop configured to co-operate with the peripheral rim of the joint socket.

9. The tool of claim 1, wherein the expanding mechanism is selected from the group consisting of a cone, and a wedge-in-wedge device.

10. The tool of claim 1, wherein the actuating device is an actuating lever.

11. The tool of claim 10, wherein the actuating lever is pivotally mounted proximally to the handle, a bearing of the lever being eccentric relative to a connection of the pull cable on the actuating lever so that the connection of the pull cable can be brought into two stable over-dead-center positions relative to the bearing of the actuating lever.

12. The tool of claim 11, wherein the actuating lever is adapted to be brought into a position parallel to the connecting element and can be generally fixed in said position via a locking mechanism when the joint socket holder is in the expanded position.

13. The tool of claim 12, wherein the locking mechanism associated with the actuating lever comprises a bolt adapted to be engaged in a notch formed on the actuating lever, the bolt biased into the locking position by a compression spring or other resilient element.

14. The tool of claim 1, wherein the at least one expandable element is movable into an expanded position against the action of a spring, a spring that exerts a force in the radial direction or another resilient element.

15. The tool of claim 1, wherein the one or more projections form counterparts to complementary radial recesses in the form of equatorially extending grooves on the inner side of the joint socket.

16. The tool of claim 1, wherein the tool is associated with at least one marker which is contactlessly or otherwise detectable, by means of an associated measurement value ascertainment system.

17. The tool of claim 16, wherein at least one marker has retro-reflecting spheres or other optical elements.

18. The tool of claim 17, wherein at least one marker comprises elements selected from the group consisting of magnetic elements, electromagnetic, magnetic and electromagnetic elements.

19. The tool of claim 16, wherein at least one marker is arranged on the handle.

20. The tool of claim 1, wherein the actuation of the expanding mechanism is effected by the exertion of a force which changes direction at least to some extent in the course of its transmission.

21. The tool of claim 1 in combination with a position-determining or navigation device.

22. The tool of claim 1, wherein a central longitudinal axis of the joint socket holder is generally aligned with a central longitudinal axis of the handle.

23. The tool of claim 1, wherein the joint socket holder is generally accessible for cleaning thereof.

24. The tool of claim 1, wherein the joint socket is coupled to the artificial joint without cement.

25. The tool of claim 1, wherein the joint socket is coupled to the artificial joint via a press-fit connection.

26. A position-determining device for ascertaining the position of a joint socket of an artificial joint or the position of an artificial joint, wherein said device comprises:
- a tool for placing or removing joint sockets or joints, the tool comprising:
  - means for holding a joint socket;
  - an eccentric over-dead-center means for actuating the means for holding, the over-dead-center means having two over-dead-center positions; and
  - an arcuate connection member connecting the means for holding to the over-dead-center means, the arcuate connection member comprising one or more openings;
- means for ascertaining the position and alignment of the tool; and
- means for evaluating the acquired data.

27. The device of claim 26, further comprising a memory for storing information selected from the group consisting of the acquired data, the evaluated data, reference values, specific data in respect of the spatial position of a bone structure of the recipient, and any two or more of the said types of information.

28. The device of claim 26, wherein a comparison device is provided which compares the actual position of the joint socket of an artificial joint and the position of a recess in the bone of the recipient provided therefor and provides corresponding navigation directions.

29. The device of claim 26, wherein the means for ascertaining the position and alignment of the tool comprises means for ascertaining markers selected from the group consisting of optical markers, magnetic markers, electromagnetic markers, and any two or more of said types of marker.

30. The device of claim 26, wherein the means for ascertaining the position and alignment of the tool comprises a stereo-camera.

31. A method for implanting a joint socket implant of an artificial joint, the method comprising:
- inserting a joint socket holder in a concave cavity of the joint socket implant;
- engaging and disengaging an inner surface of the socket implant with at least one expanding element of the joint socket holder, the expanding element being actuated by a force transmission member held in an over-dead-center position relative to a rotational center of an actuator coupled to the force transmission member during both of the engaging and disengaging steps;
- implanting the joint socket implant in an operating site on a bone of a patient while maintaining a substantially unobstructed view of the operating site.

32. The method of claim 31, wherein engaging an inner surface of the socket implant includes applying a force radially outward onto said inner surface with the at least one expanding element.

33. The method of claim 32, wherein the force transmission member is held in an over-dead-center position when applying the force.

34. The method of claim 31, wherein implanting the joint socket implant is performed in a minimally invasive manner and further comprises ascertaining the position and alignment of the joint socket holder.

35. The method of claim 34, wherein ascertaining the position and alignment of the joint socket holder includes detecting the position of a marker on a tool comprising the joint socket holder.

* * * * *